(12) United States Patent
Cinbis

(10) Patent No.: US 9,095,284 B2
(45) Date of Patent: Aug. 4, 2015

(54) DISTANCE MEASUREMENT USING IMPLANTABLE ACOUSTIC TRANSDUCERS

(75) Inventor: Can Cinbis, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 1316 days.

(21) Appl. No.: 12/914,616

(22) Filed: Oct. 28, 2010

(65) Prior Publication Data

US 2012/0109012 A1    May 3, 2012

(51) Int. Cl.
*A61B 5/107*   (2006.01)
*A61N 1/365*   (2006.01)
*A61B 8/00*    (2006.01)
*A61N 1/368*   (2006.01)
*A61B 5/00*    (2006.01)
*A61N 1/362*   (2006.01)

(52) U.S. Cl.
CPC .......... *A61B 5/1076* (2013.01); *A61B 8/56* (2013.01); *A61N 1/36528* (2013.01); *A61B 5/686* (2013.01); *A61B 5/6869* (2013.01); *A61B 2562/06* (2013.01); *A61N 1/368* (2013.01); *A61N 1/3627* (2013.01); *A61N 1/36578* (2013.01)

(58) Field of Classification Search
CPC .... A61B 5/1072; A61B 5/1076; A61N 1/362; A61N 1/368
USPC .......... 600/586, 587, 439, 300, 301, 584, 508, 600/504
See application file for complete search history.

(56) References Cited

U.S. PATENT DOCUMENTS

| | | | |
|---|---|---|---|
| 5,779,638 A | 7/1998 | Vesely et al. | |
| 5,795,298 A | 8/1998 | Vesely et al. | |
| 5,830,144 A | 11/1998 | Vesely | |
| 7,228,175 B2 | 6/2007 | Jain et al. | |
| 7,233,821 B2 | 6/2007 | Hettrick et al. | |
| 7,344,493 B2 | 3/2008 | Sonnenschein et al. | |
| 7,406,351 B2 | 7/2008 | Wesselink | |
| 7,610,078 B2 | 10/2009 | Willis | |
| 7,729,764 B2 | 6/2010 | Hettrick et al. | |
| 2003/0158494 A1 | 8/2003 | Dahl et al. | |
| 2004/0176810 A1 | 9/2004 | Stadler et al. | |
| 2005/0027323 A1 | 2/2005 | Mulligan et al. | |
| 2006/0224088 A1 | 10/2006 | Roche | |
| 2006/0224203 A1 | 10/2006 | Hettrick et al. | |
| 2010/0010354 A1 | 1/2010 | Skerl | |

FOREIGN PATENT DOCUMENTS

WO    WO 00/69490 A1    11/2000

OTHER PUBLICATIONS

International Search Report and Written Opinion for PCT application No. PCT/US2011/034535, Aug. 26, 2011, 9 pgs.

*Primary Examiner* — Max Hindenburg
(74) *Attorney, Agent, or Firm* — Michael C. Soldner

(57) ABSTRACT

Implantable systems and methods (e.g., using an implantable medical device) for measuring distance including a transmit/receive acoustic transducer implantable at a first location for transmitting and receiving acoustic signals, an echo acoustic transducer implantable at a second location for receiving the acoustic signal from the transmit/receive acoustic transducer and in response thereto transmitting a return echo signal to be received by the transmit/receive acoustic sensor, and a controller to control transmission of the acoustic signal from the transmit/receive acoustic transducer at a transmit time and determine a receive time corresponding to the time the transmit/receive acoustic transducer receives the return echo signal. The distance between the transmit/receive acoustic transducer and the echo acoustic transducer is determined as a function of the transmit time and the receive time.

19 Claims, 8 Drawing Sheets

DISTANCE MEASUREMENT USING IMPLANTABLE ACOUSTIC TRANSDUCERS

The disclosure herein relates to distance measurement using implantable acoustic transducers (e.g., measurement of body organs using an implantable medical device).

Measurement of distances within the body, e.g., measurement of organ dimensions such as dimensions of the heart, bladder, stomach, etc., have many applications. For example, such measurements may be used in disease management, e.g., such as heart failure management, management of urinary incontinence, and/or management of obesity. With respect to heart management, for example, measurement of left ventricular dimension in the heart is a valuable indication for understanding the evolution of heart failure. For example, if left ventricular volume is increasing over time, such an increase may be indicative of deteriorating heart disease state. Further, for example, with drug or cardiac resynchronization therapy (CRT), a decreasing left ventricular dimension may be an indication of therapy efficacy. A wide variety of patient therapies exist that may benefit from such distance measurements, e.g., stimulation therapies, drug delivery therapies, incontinence therapies, etc. In other words, certain therapies may be delivered based in some manner on such distance measurements.

Conventionally, for example, for research purposes, implantable sonomicrometer distance measurement devices (e.g., small bead-shaped ultrasound crystals or sonomicrometer piezoelectric crystals) have been implanted in desired locations and a transmitting crystal driven externally (e.g., via an external device) with a pulse generator. When the propagating pulse from the transmitting crystal reaches another crystal (e.g., the receiving crystal), an amplified signal is typically envelope detected and rectified, and a threshold detector provides an output marking the arrival time of the pulse. Since the external device knows when the transmit pulse was triggered (e.g., when the transmitting crystal was driven to generate the pulse), delta time, $\Delta t$ between the time of arrival of the received pulse by the receiving crystal and time of transmission of the transmit pulse by the transmitting crystal can be computed. Assuming the speed of sound, velocity of the signal $V_{sound}$ in the human body is relatively constant at around 1550 m/s, then the distance "d" between the two crystals (e.g., transducers) can be calculated from: $d=V_{sound} \times \Delta t$. This technique is typically referred to as sonomicrometry and has been used for measuring heart chamber volumes (e.g., in calculating pressure-volume (PV) loops). For example, such techniques are described in, U.S. Pat. No. 7,233,821 to Hettrick et al., issued 19 Jun. 2007 and entitled "Method and Apparatus for Evaluating Ventricular Performance During Isovolumic Contraction" and, for example, U.S. Patent Application Publication No. US2005/0027323 to Mulligan et al., published Feb. 3, 2005 and entitled "Implantable Medical Device for Monitoring Cardiac Blood Pressure and Chamber Dimension."

However, such conventional configurations for measuring distance require, for example, both the transmitting crystal and the receiving crystal to be connected (e.g., by a wire to both transmit and receive crystals) such that the transmit pulse time from the transmitting crystal relative to arrival time of the received pulse at the receiving crystal can be measured. Such connected transmit and receive crystals, for example, of a chronic implantable medical device that include such components, may increase complexity of the surgical implant procedure for the implantable medical device, may require complicated implant tools, and the integrity of a wired connection of such crystals over time may be a reliability issue.

SUMMARY

The disclosure herein relates generally to systems and methods for measuring distances via implantable sensors using ultrasound. For example, such systems and devices may measure distances (e.g., organ dimensions) for use with therapy, and further, may initiate or adjust therapy based on such measurements.

An exemplary implantable medical device measurement system described herein includes a transmit/receive acoustic sensor and an echo acoustic sensor. The transmit/receive acoustic sensor includes a transmit/receive acoustic transducer implantable at a first location (e.g., wherein the transmit/receive acoustic transducer may be configured to transmit and receive acoustic signals) and the echo acoustic sensor (e.g., a wireless sensor) includes an echo acoustic transducer implantable at a second location (e.g., wherein the echo acoustic transducer may be configured to receive an acoustic signal from the transmit/receive acoustic transducer and in response thereto transmit a return echo signal to be received by the transmit/receive acoustic transducer). Further, the system includes a controller configured to control transmission of the acoustic signal from the transmit/receive acoustic transducer at a transmit time and determine a receive time corresponding to the time the transmit/receive acoustic transducer receives the return echo signal transmitted by the echo acoustic transducer. The controller is further configured to determine a distance between the transmit/receive acoustic transducer and the echo acoustic transducer as a function of the transmit time and the receive time.

An exemplary implantable medical device method as described herein for measuring distance using implantable acoustic transducers includes implanting a transmit/receive acoustic transducer at a first location (e.g., wherein the transmit/receive acoustic transducer is configured to transmit and receive acoustic signals); implanting an echo acoustic transducer at a second location (e.g., wherein the echo acoustic transducer is configured to receive an acoustic signal from the transmit/receive acoustic transducer and transmit a return echo signal in response thereto to be received by the transmit/receive acoustic transducer); transmitting an acoustic signal from the transmit/receive acoustic transducer at a transmit time; detecting, using the echo acoustic transducer, the acoustic signal transmitted by the transmit/receive acoustic transducer and transmitting a return echo signal to be received by the transmit/receive acoustic sensor; and receiving, using the transmit/receive acoustic transducer, the return echo signal transmitted by the echo acoustic transducer at a receive time. A distance between the transmit/receive acoustic transducer and the echo acoustic transducer is determined as a function of the transmit time and the receive time.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
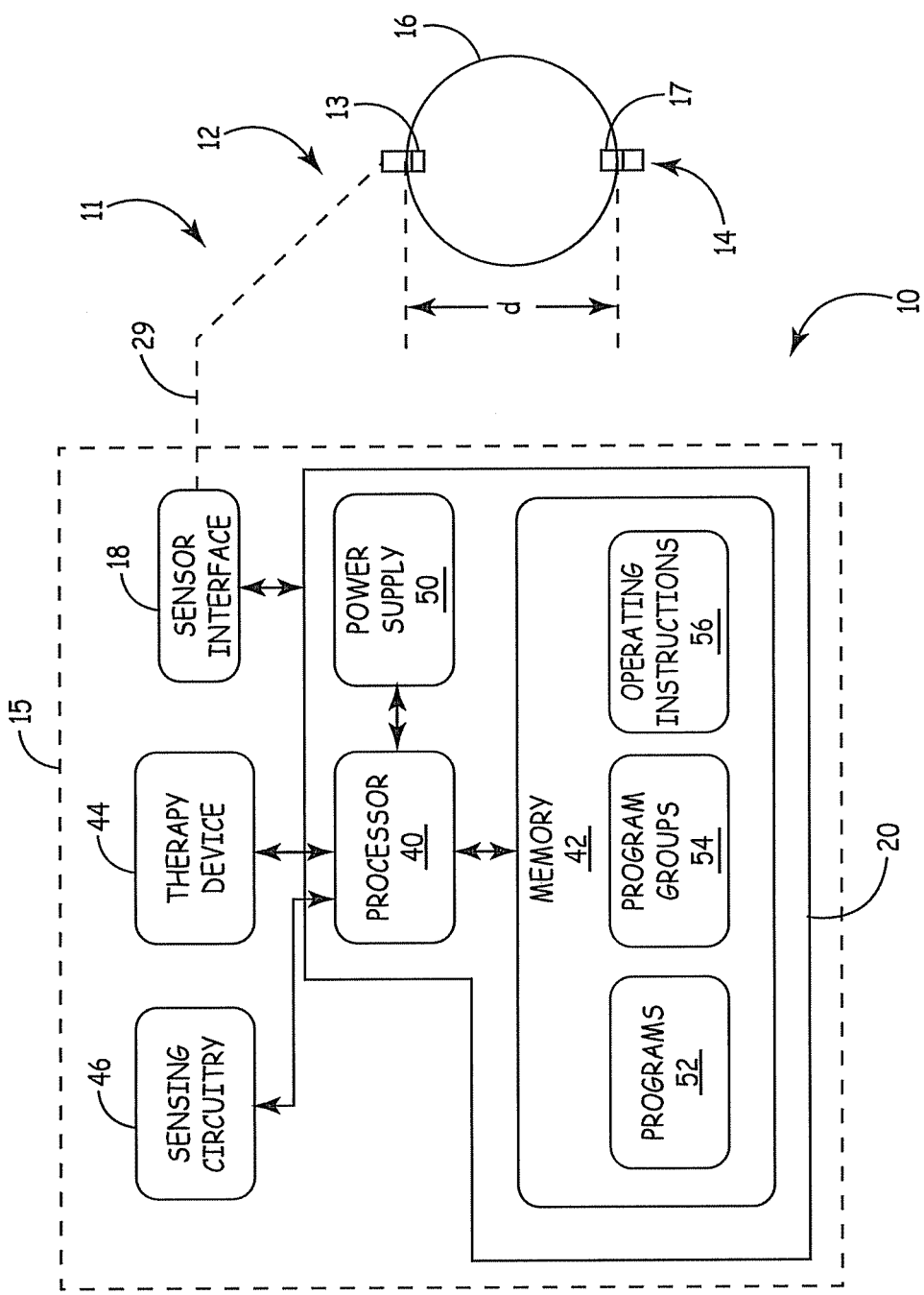
FIG. 1 is a general diagram illustrating an example implantable measurement system, upon which delivery of a therapy to a patient may be based.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods and systems shall be described with reference to FIGS. 1-8. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the process steps and the size and shape of various elements herein may be modified but still fall within the scope of the present disclosure, although certain timing, one or more shapes and/or sizes, or types of elements, may be advantageous over others.

The methods described herein are intended to illustrate the general functional operation of the devices and/or systems described herein, and should not be construed as reflective of a specific form of software or hardware necessary to practice one or more of the methods described herein. It is believed that the particular form of software will be determined primarily by the particular system architecture employed in a device (e.g., an implantable medical device) and/or system and/or by the particular detection and therapy delivery methodologies employed by the device and/or system. Providing software to accomplish the described methods in the context of any modern medical device, given the disclosure herein, is within the abilities of one of skill in the art.

FIG. 1 is a general diagram illustrating an example measurement system 10 that, may, for example, be used as part of an implantable medical device 15 for the delivery of therapy to a patient. At least in one embodiment, the system is an implantable system. In such an implantable system (where one or more of the components thereof are implanted) electronic component size should be reduced as well as reducing power consumption (e.g., so that a small size battery can provide needed peak power and longevity).

One embodiment of a method or system that may accomplish one or more of such goals is to use an echo acoustic sensor (e.g., including a sonomicrometry piezoelectric crystal) designed to bounce a pulse (e.g., immediately) when the echo acoustic sensor detects a pulse from a transmit/receive acoustic sensor (e.g., including a sonomicrometry piezoelectric crystal). The transmit/receive acoustic sensor can then listen for the return echo pulse emitted from the echo acoustic sensor for use in measuring the distance therebetween. In other words, for example, the total time delay from transmit time of the original pulse to the time of receiving the return echo pulse will be twice the time of signal propagation from the implanted acoustic transducer of transmit/receive acoustic sensor to the implanted acoustic transducer of the echo acoustic sensor. As such, for example, assuming the speed of sound, velocity of the signal $V_{sound}$ in the human body is relatively constant at around 1550 m/s. Then, the distance "d" between the two sensors (e.g., sonomicrometry piezoelectric crystals) can be calculated from: $d = V_{sound} \times \Delta t/2$, wherein $\Delta t$ is the time delay from the time of transmission from the implanted acoustic transducer of transmit/receive acoustic sensor to the time of receipt of the return echo pulse from the echo acoustic sensor by the implanted acoustic transducer of the transmit/receive acoustic sensor. In case there is a substantial fixed delay "$t_d$" in the echo acoustic sensor from its reception of the acoustic pulse from the transmit/receive acoustic sensor to transmission of the return echo pulse, the distance "d" between the two sensors can be calculated from: $d = V_{sound} \times (\Delta t - t_d)/2$. For example, the measurement of the varying time delay $\Delta t$ may be provided by subtraction of arrival time of the received echo from the transmit time of transmit pulse. Alternatively, for example, a digital counter or analog integrator can be started at the transmit time of the transmit pulse from the transmit/receive acoustic sensor and stopped at the receive time with the arrival of the received echo by the transmit/receive acoustic sensor.

Exemplary measurement system 10 as shown in FIG. 1 includes measurement sensor apparatus 11, controller 20, and a therapy device 44, which may be part of a medical device 15 (e.g., an implantable medical device). In the example shown in FIG. 1, therapy device 44 may include any therapy devices that may benefit from the measurements provided using measurement sensor apparatus 11.

For example, the therapy device may be, or the components of system 10 may be a part of, a variety of implantable medical devices for delivering a therapy and/or monitoring one or more physiologic conditions of patients. For example, such implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for delivery of stimulation or sensing. For example, electrodes or sensors may be located at a distal portion of the lead. A proximal portion of the lead may be coupled to an implantable medical device housing, which may contain electronic circuitry such as stimulation generation and/or sensing circuitry.

Further, for example, the implantable medical devices, such as cardiac pacemakers or implantable cardioverter defibrillators, may provide therapeutic stimulation to the heart by delivering electrical therapy signals such as pacing pulses, or cardioversion or defibrillation shocks, via electrodes of one or more implantable leads. In some cases, such an implantable medical device may sense for intrinsic depolarizations of the heart, and control the delivery of such signals to the heart based on the sensing. When an abnormal rhythm is detected, such as bradycardia, tachycardia or fibrillation, an appropriate electrical signal or signals (e.g., in the form of pulses) may be delivered to restore the normal rhythm. For example, in some cases, an implantable medical device may deliver pacing, cardioversion or defibrillation signals to the heart of the patient upon detecting ventricular tachycardia, and deliver cardioversion or defibrillation electrical signals to a patient's heart upon detecting ventricular fibrillation.

Yet further, for example, the implantable medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation or delivery of pharmaceutical agent, insulin, pain relieving agent or anti-inflammatory agent to a target tissue site within a patient. A medical device may be used to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes. In some cases, the electrical stimulation may be used for muscle stimulation, e.g., functional electrical stimulation (FES) to promote muscle movement or prevent atrophy. In some therapy systems, an implantable electrical stimulator delivers electrical therapy to a target tissue site within a patient with the aid of one or more medical leads that include electrodes. In addition to or instead of electrical stimulation therapy, a medical device may deliver a therapeutic agent to a target tissue site within a patient with the aid of one or more fluid delivery elements, such as a catheter.

One or more of the acoustic sensors or portions thereof used herein for distance measurement may be implanted as part of a lead used to sense or provide therapy. For example, in one embodiment, the transducers described herein may include sonomicrometer crystals. The sonomicrometer crystals can each be formed as a cylindrical piezoelectric crystal tube sandwiched between an inner tubular electrode and an outer tubular electrode and fitted around a lead body such as described in U.S. Pat. No. 5,795,298. Various sonomicrometer systems, including piezoelectric crystals acting as a transmitter of ultrasonic energy and/or a receiving piezoelectric crystal that vibrates and provides an output signal when exposed to the ultrasonic energy, are described in U.S. Pat. No. 5,779,638, U.S. Pat. No. 5,795,298, and U.S. Pat. No. 5,830,144, all of which are incorporated in their entirety herein by reference.

In other words, processes described herein may be implemented by various devices (e.g., implantable medical devices) and systems. Such devices and systems may include one or more leads, electronic circuits, power sources, sensors, electrodes, fluid delivery devices, etc. Further, such devices and systems may be configured to monitor one or more physiological parameters of a patient, e.g., electrical activity of a patient's heart, chemical activity of a patient's heart, chemical activity or pressure levels of a patient's gastrointestinal (GI) system, hemodynamic activity of a patient's heart, electrical activity of a patient's muscles, and electrical activity of a patient's nerves (e.g., vagus nerve, splanchnic nerves, etc.).

As shown in FIG. 1, controller 20 may include a processor 40, memory 42, and power source 50. Controller 20 is coupled to and may control therapy device 44 based on measurements made according to one or more measurement processes described herein.

Memory 42 includes computer-readable instructions that, when executed by processor 40, cause controller 20 and/or the system including controller 20 to perform various functions. Memory 42 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 42 may include programs 52, program groups 54, and operating instructions 56 in separate memories within memory 42 or separate areas within memory 42. Each program 52 may define a particular process (e.g., such as a program of therapy in terms of respective values for electrical stimulation parameters, such as electrode combination, electrode polarity, current or voltage amplitude, pulse width and pulse rate; or a program to control and perform measurements according to one or more processes described herein, such as, for example, those for measuring distance between crystals). A program group 54 defines a group of programs that may be delivered together on an overlapping or non-overlapping basis. Operating instructions 56 guide general operation of the system 10 under control of processor 40.

Processor 40 may control therapy device 44 according to programs 52 and program groups 54 stored in memory 42 to apply particular therapies (e.g., stimulation, drug delivery, warnings, bladder control therapy, etc.). Further, processor 40 may also receive sensor inputs (e.g., representative of one or more physiological parameters of a patient, such as electrical activity of a patient's heart, chemical activity of a patient's heart, chemical activity or pressure levels of a patient's gastrointestinal (GI) system, hemodynamic activity of a patient's heart, electrical activity of a patient's muscles, and electrical activity of a patient's nerves, etc.) via sensor circuitry 46 in addition to distance measurements made by one or more processes described herein. Processor 40 may include a microprocessor, a controller, a digital signal processor (DSP), an application specific integrated circuit (ASIC), a field-programmable gate array (FPGA), or equivalent discrete or integrated digital or analog logic circuitry, and the functions attributed to processor 40 herein may be embodied as software, firmware, hardware or any combination thereof.

The techniques described in this disclosure, including those attributed to measurement system 10, medical device 15, or other various components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" or "controller" or "control circuitry" may generally refer to any of the foregoing circuitry, alone or in combination with other circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

Further, methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The hardware used to the accomplish the described methods, may include any one or more of a microprocessor, a digital signal processor (DSP), a controller, an application specific integrated circuit (ASIC), a field programmable gate array (FPGA), or equivalent discrete or integrated logic circuitry. In one or more exemplary embodiments, the processor may include multiple components, such as any combination of one or more microprocessors, one or more controllers, one or more DSPs, one or more ASICs, or one or more FPGAs, as well as other discrete or integrated logic circuitry. The functions and processes described herein may be embodied as software, firmware, hardware, or any combination thereof. As used herein, the term "circuitry" may be implemented in software as executed by one or more processes, firmware, hardware, or any combination thereof.

Various components of the system 10 are coupled to power supply 50, which may include a rechargeable or non-rechargeable battery. A non-rechargeable battery may be selected to last for several years, while a rechargeable battery may be inductively charged from an external device, e.g., on a daily or weekly basis. In other examples, power supply 50 may be powered by proximal inductive interaction with an external power supply carried by a patient.

Processor 40 also controls operation of measurement sensor apparatus 11 used to provide distance measurements. Measurement sensor apparatus 11, as shown in FIG. 1, includes a transmit/receive acoustic sensor 12 and an echo acoustic sensor 14. The transmit/receive acoustic sensor 12 includes a transmit/receive transducer 13 that may be any acoustic transducer implantable at a first location (e.g., a location of an object or tissue) and is operable to transmit an acoustic signal in medium at the implant location and detect an acoustic signal (e.g., a return echo acoustic signal).

For example, the transmit/receive acoustic transducer 13 may include a sonomicrometry piezoelectric crystal that generates an acoustic signal based on an electrical signal applied thereto and detects an acoustic signal and converts the detected acoustic signal into an electrical signal for sensing by receiver components of the sensor 12. For example, the sonomicrometer piezoelectric crystal, such as lead zirconate titanate (PZT) and polyvinylidene fluoride (PVDF), may be driven by an electrical signal to produce an acoustic signal, and further, an acoustic pulse detected by the crystal (resulting in an electrical signal representative thereof) may be envelope detected and rectified, and a threshold detector may be used to establish the existence of a valid detected pulse. Further, for example, other acoustic sensors that include capacitive micromachined ultrasound transducers (CMUT) and magnetostrictive transducers or combinations thereof may be used.

The echo acoustic sensor 14 includes an echo acoustic transducer 17 implantable at a second location (e.g., a location of an object or tissue) and is operable to detect an acoustic signal transmitted by the transmit/receive acoustic sensor 12 and generate a return echo signal in response thereto. For example, the echo acoustic transducer 17 may include a sonomicrometry piezoelectric crystal (e.g., such as PZT or PVDF) that is configured to detect presence of an acoustic signal from the transmit/receive acoustic sensor 12 and generate a return echo signal in response to the detected acoustic signal. Further, for example, other acoustic sensors that include capacitive micromachined ultrasound transducer (CMUT) and magnetostrictive transducer, and combinations thereof, may be used.

The configuration (e.g., functionally and/or physically) of the echo acoustic sensor 14 will depend upon the application of such a sensor. For example, if the echo acoustic sensor resides inside a tubular anatomy such as blood vessels or urinary tract, a cylindrical shape may be used. Further, for example, if the echo acoustic sensor is placed epicardially, a flat pancake shape may be used. Such piezoelectric materials are available in a variety of shapes (e.g., disk, cylindrical, cylindrical annulus, doughnut, spherical, etc.) and the disclosure herein is not limited to any particular shape, although one shape may be more beneficial over others for particular applications. In one or more applications, such an echo acoustic sensor 14 may be delivered by a catheter, and as such, may be either actively or passively fixated at a particular location. For example, active fixation may be accomplished using a screw or tines that may or may not penetrate tissue. If devices are surgically attached, they may, for example, be sutured in place.

Figure 8:
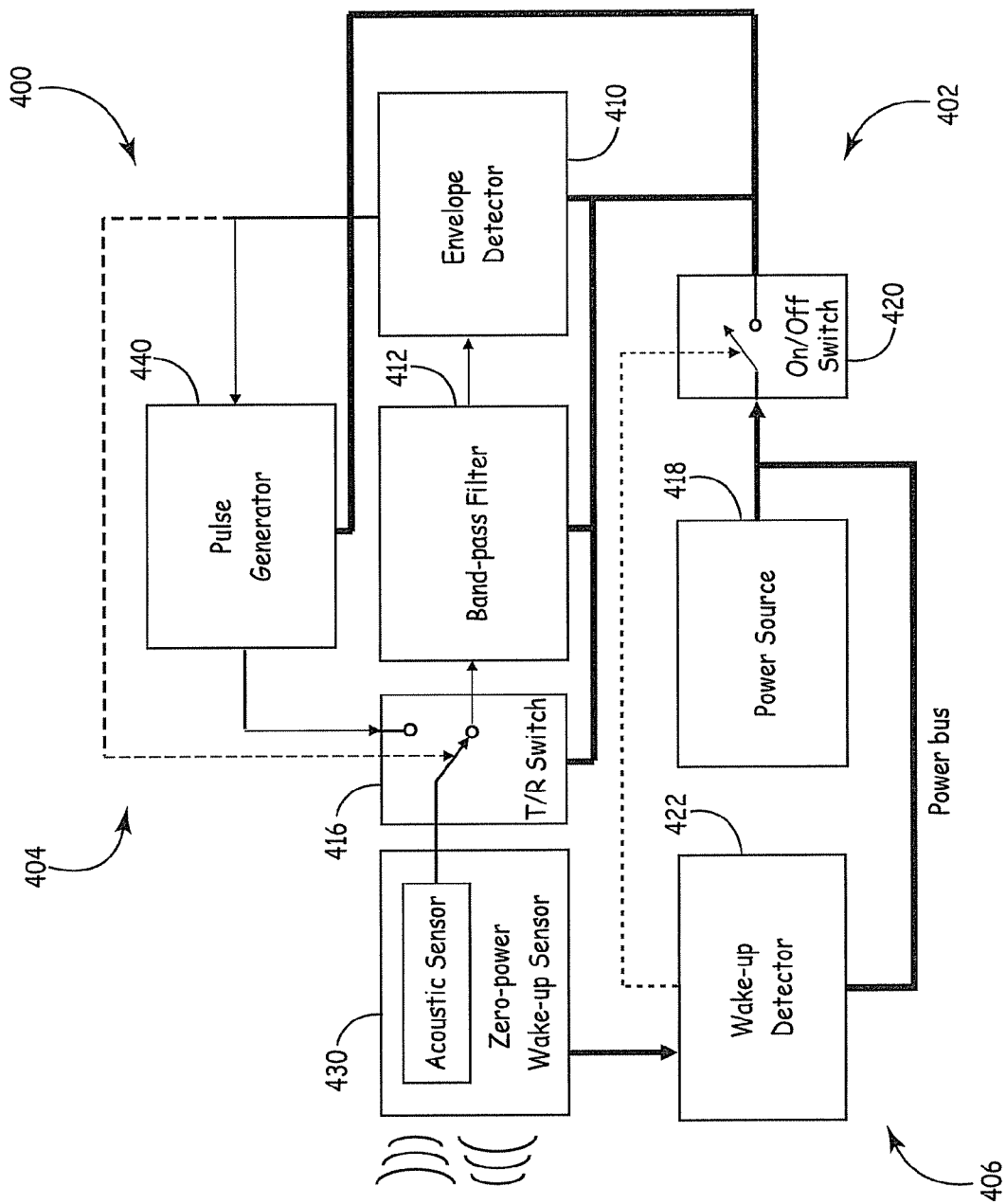
FIG. 8 is a functional block diagram of one embodiment of an echo acoustic sensor that may be used in a measurement system, such as shown in FIG. 1.

A functional block diagram of one embodiment of an echo acoustic sensor, such as echo acoustic sensor 14, is shown in FIG. 8. For example, the echo acoustic sensor 400 of FIG. 8 may include detection circuitry 402 for detecting an acoustic signal transmitted by the transmit/receive acoustic transducer 13 and transmit circuitry 404 to generate a return echo signal in response thereto. For example, the detection circuitry 402 may include wakeup circuitry 406 (described further herein with respect to one or more measurement processes) for waking the sensor up to listen for an acoustic signal from acoustic transducer 13, may include band-pass filters 412 to select particular frequency bands, amplifiers to amplify RF signal (not shown), and an envelope detector 410 to detect an incoming RF pulse (e.g., the T/R switch 416 being operated by the envelope detector 410; the T/R switch in default state being in the receive position). Further, the transmit circuitry may include circuits such as RF pulse generator 440 for driving, for example, the acoustic transducer 17 (e.g., automatically upon determination of a valid received pulse from the acoustic transducer 13 such as with use of the envelope detector). For example, the T/R switch may be put into the transmit state for sending an echo pulse back to the transmit/receive acoustic sensor when a valid incoming pulse is received). Further, for example, the echo acoustic sensor 400 may include power circuitry 418 for energizing the circuitry of the sensor 400. For example, such power circuitry 418 may include power harvesting circuitry to trickle charge an internal power source, may include inductive/acoustic power coupling circuitry to generate power from a distant intracorporeal or extracorporeal power source to charge its internal power source or without an internal power source to start operating immediately as long as external power is provided, etc.

The controller 20 may control the transmission of the acoustic signal from the transmit/receive acoustic transducer sensor 13 at a transmit time and determine a receive time corresponding to the time the transmit/receive acoustic transducer receives a return echo signal transmitted by the echo acoustic transducer 17 via the sensor interface 18 (e.g., which forms a part of sensor 12 but which may include circuitry that is not co-located therewith). For example, the sensor interface 18 may be part of the sensor 12 and implanted at the first location or be part of circuitry located with the controller 20. The sensor interface 18 receives control signals from controller 20 and is used to drive the transmit/receive acoustic transducer 13, as well as receiving circuitry for detecting the return echo acoustic signal.

The controller 20 is further configured to determine a distance between the transmit/receive acoustic transducer 13 and the echo acoustic transducer 17 as a function of the transmit time and the receive time. For example, the distance between the transmit/receive acoustic transducer 13 and the echo acoustic transducer 17 may be determined using the relationship of distance $d = V_{sound} \times \Delta t/2$, where $\Delta t$ is the time between the transmit time and the receive time, and $V_{sound}$ is the velocity of the acoustic signals traveling between transmit/receive acoustic transducer 13 and the echo acoustic transducer 17.

The transmit/receive acoustic transducer 13 (and/or other implantable portions of acoustic sensor 12) may be connected to the controller by a wire connection 29, or may be wireless components capable of communication with controller 20 for performing distance measurements. Power for the transmit/receive acoustic transducer 13 may be provided by the same power source 50 as powers the controller 20 (e.g., via line connection 29) and/or may be energized by one or more other sources of power. For example, such power may be inductively or acoustically coupled to the sensor 12 from an external source, either during acoustic measurements, or to charge a self-contained power supply of the sensor 12. Further, for example, acoustic sensor 12 may have its own power harvesting circuitry to harvest power from internal sources of energy such as kinetic energy due to motion, flow, thermal gradient, etc. that can be stored in a power source until the time of measurements.

Likewise, echo acoustic sensor 14 may include power circuitry to provide power to allow the echo acoustic sensor 14 to detect the receipt of the acoustic signal from the transmit/receive acoustic transducer 13 and to transmit the return echo signal in response thereto. For example, such power may be provided by battery or rechargeable battery, may be inductively or acoustically coupled to the sensor 14 using an external source, may be provided via RF coupling techniques, may be provided by a power harvesting system that can utilize power from internal sources of energy such as kinetic energy due to motion, flow, thermal gradient, etc. that can be harvested and stored in an internal power source until the time of measurements, etc.

Figures 2A, 2B:
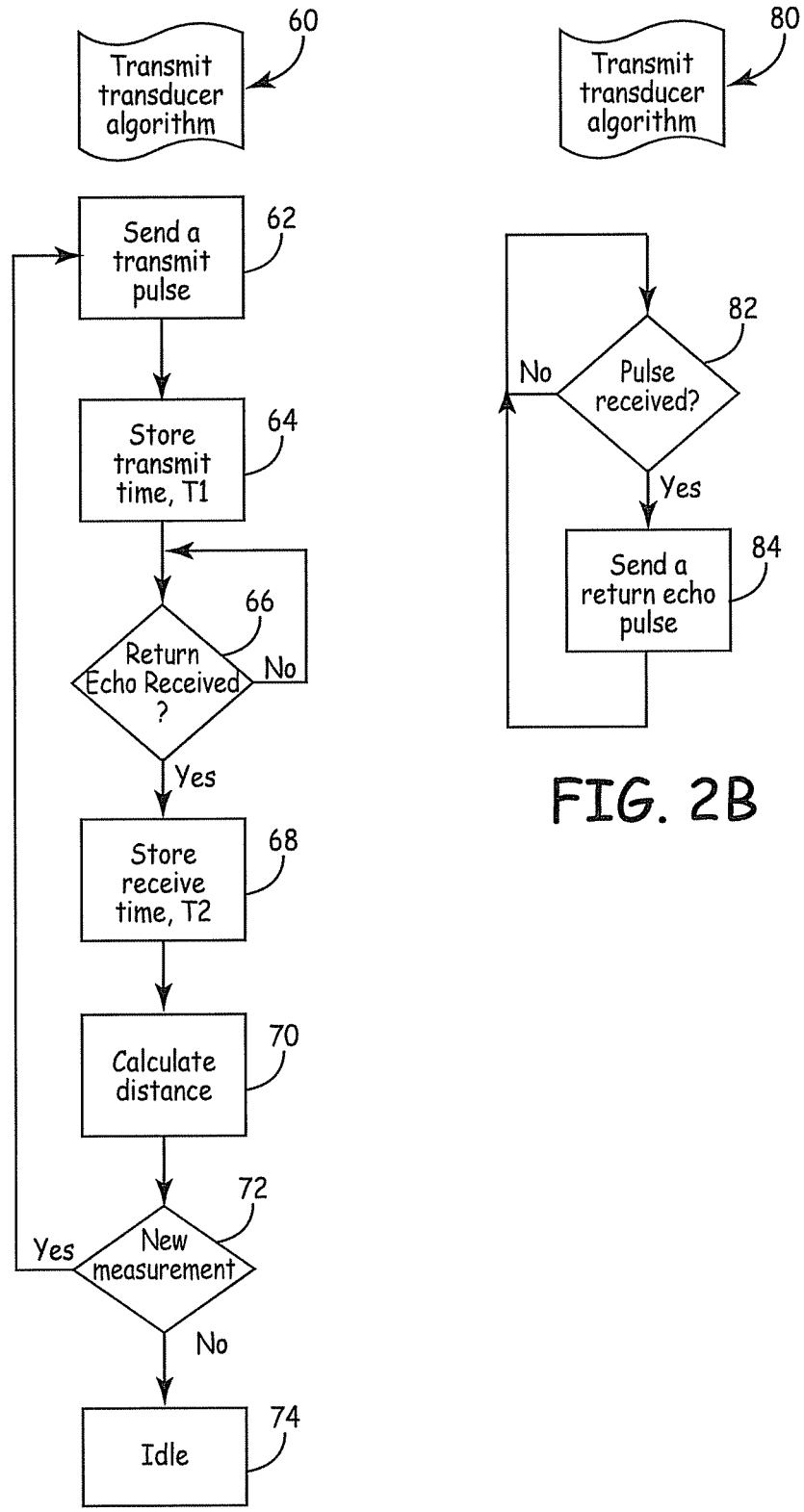
FIGS. 2A-2B depict two flow diagrams of an acoustic measurement process that may be implemented using a system such as shown in FIG. 1.
Figure 3:
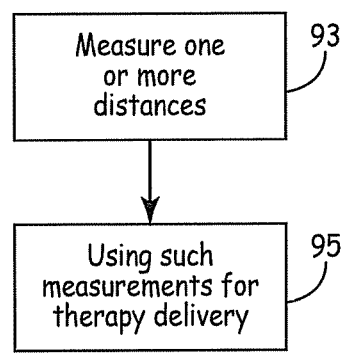
FIG. 3 is a general flow diagram showing the process of using the distance measurements, such as those made using the processes shown in FIGS. 2A-2B, in therapy delivery.

FIGS. 2A and 2B depict two flow diagrams of an acoustic measurement process that may be implemented using a system such as shown in FIG. 1 under control of, for example, controller 20. FIG. 2A shows a transmit/receive algorithm 60 carried out using the transmit/receive acoustic transducer 13 and FIG. 2B shows an echo algorithm 80 carried out using the echo acoustic transducer 17.

As shown in FIG. 2A, an acoustic pulse is transmitted (block 62) such as by transmit/receive acoustic transducer 13 under control of controller 20 (e.g., execution of one or more instructions). The time of transmission (T1) is stored (block 64) in memory of controller 20.

As shown in the echo algorithm 80 of FIG. 2B, for example, the echo acoustic sensor 14 is configured to listen for and determine whether a pulse has been transmitted (block 82) (e.g., by transmit/receive acoustic transducer 13). If the echo acoustic sensor 14 detects the transmitted pulse, then a return echo pulse is caused to be transmitted by the echo acoustic transducer 17 (block 84). If the echo acoustic sensor 14 does not detect a transmitted pulse, then it keeps listening. Further, after the return echo pulse is caused to be transmitted by the echo acoustic transducer 17 (block 84), then the echo acoustic sensor 14 continues to listen for additional acoustic pulses from transmit/receive acoustic transducer 13.

For power conservation, an echo acoustic transducer may be equipped with a zero or low-power wake up feature (e.g., as may be implemented using the zero-power wake up circuitry 430 and wakeup detector 422 as shown in FIG. 8, as part of the wakeup circuitry 406). This may be implemented via radiated RF, conducted current, near-field inductive or via existing acoustic link. For example, for low-power wake up, the echo acoustic sensor may periodically wake up from a zero or ultra-low current state to look for a signal to wake up. If it detects a wake up signal via one of these exemplary methods, it goes into the operating mode for listening for the acoustic pulse from the acoustic sensor 12 and echoing back. To go back to zero or ultra-low current state, echo acoustic sensor may use a time-out scheme or can be instructed remotely to do so using the same physical means employed for wake up. For zero-power wake up, the signal received by the echo acoustic transducer 14 should be large enough (e.g., such as a few hundreds of millivolts) to be detected by electronic circuitry with active electronics in zero or near zero current drain static state. For example, as shown in FIG. 8, wakeup detector 422 is configured to operation On/Off switch 420 for connection of power to the other echo acoustic sensor components.

As further shown in the transmit/receive algorithm 60 of FIG. 2A, after the acoustic pulse is transmitted by the transmit/receive acoustic transducer 13, the transmit/receive acoustic sensor 12 is configured to listen for and determine whether a return echo pulse has been transmitted by the echo acoustic transducer 17 in response to the pulse transmitted by the transmit/receive acoustic transducer 13 (block 66). If the transmit/receive acoustic sensor 12 detects the return echo pulse, then the receive time (T2) of the pulse is stored in memory (block 68). If the transmit/receive acoustic sensor 12 does not detect a transmitted return echo pulse from echo acoustic transducer 17, then it keeps listening.

The return echo pulse caused to be transmitted by the echo acoustic transducer 17 is of a strength that is easily detected by transmit/receive acoustic sensor 12. For example, the acoustic signal strength of the return echo pulse is greater than the strength of the reflected acoustic echo signal that may be returned to the transmit/receive acoustic transducer 13 due to reflection of the acoustic signal transmitted by the transmit/receive acoustic transducer 13 by medium (e.g., tissue) at or in proximity to the location where the echo acoustic transducer is implanted.

With the stored transmit time T1 and the stored receive time T2, the controller 20 may calculate the distance between the transmit/receive acoustic transducer 13 and the echo acoustic transducer 17 (block 70) based thereon. For example, the distance may be calculated as $d=(V_{sound})((T2-T1)/2)$.

As further shown in FIG. 2A, additional measurements may be determined, if desired (block 72). In other words, if such new measurements are desired, then another acoustic pulse is sent by transmit/receive acoustic transducer 13 and the process of detecting the pulse and generating a return echo pulse is repeated. Still further, if such new measurements are not desired, then the components for carrying out the distance measurement may be idled (block 74). In such a manner, power may be conserved. For example, performing such distance measurements on a continuous basis is possible. However, to conserve power, such measurements may also be carried out periodically or according to a programmed schedule, or, for example, upon the determination of the need for such measurements (e.g., based on sensing of one or more other physiological parameters).

Figure 7:
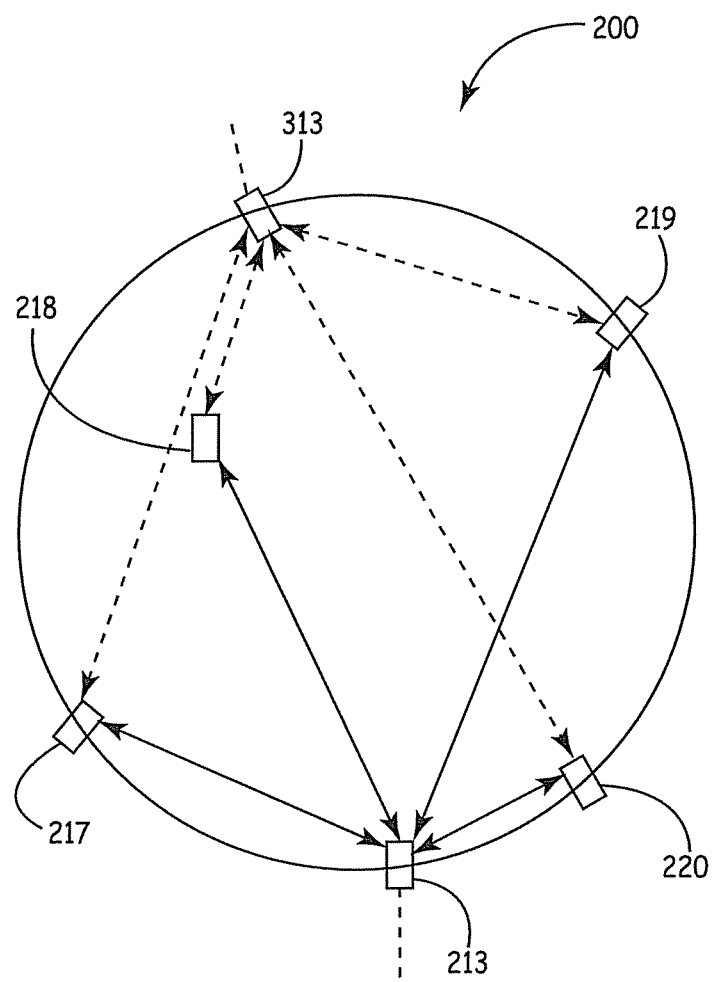
FIG. 7 is a generalized diagram illustrating the use of a plurality of acoustic sensors in a measurement system.

As shown in FIG. 7, the measurement system 10 may be expanded to include other additional transducers. For example, the system 200 shown in FIG. 7 may include multiple echo acoustic transducers 217-220 to be implanted at multiple locations. Each of the echo acoustic transducers 217-220 may be configured to receive the acoustic signal from the transmit/receive acoustic transducer 213 and in response thereto transmit a return echo signal to be received by the transmit/receive acoustic transducer 213 for use in determining a distance between the transmit/receive acoustic transducer 213 and each of the echo acoustic transducers 217-220.

In one embodiment, each of the echo acoustic transducers 217-220 that are sufficiently wide band may be configured to transmit the return echo signal at a different frequency so that the particular echo acoustic transducer whose return echo signal is being detected by the transmit/receive acoustic transducer 213 can be identified. For example, the transmit/receive acoustic transducer 213 may be associated with circuitry to receive a wideband signal and include band filters for identifying return echo signals at different frequencies corresponding to each of the echo acoustic transducers 217-220. To prevent detection of an echo pulse from an echo acoustic transducer (e.g., one of transducers 217-220) by another echo acoustic transducer (e.g., another of transducers 217-220) as a transmit pulse from transmit/receive acoustic transducer 213, different frequency bands can be reserved for transmit pulses and echo pulses.

In yet another embodiment, at the time of implant, each of the echo acoustic transducers 217-220 may be mapped to different distances and such distances noted. As a result, the return echo signal from the closest echo acoustic transducer of the echo acoustic transducers 217-220 will be detected first by the transmit/receive acoustic transducer 213. The return echo signal from the next closest echo acoustic transducer of the echo acoustic transducers 217-220 will then be detected by the transmit/receive acoustic transducer 213, and so forth. As such, using such noted differential distances of the echo acoustic transducers 217-220 from the for the transmit/receive acoustic transducer 213, it can be determined which return echo signal is being transmitted from which particular echo acoustic transducer.

Yet further, an additional transmit/receive acoustic transducer 313 may be implanted (e.g., using an implantable lead). As such, it may also transmit an acoustic pulse to the echo acoustic transducers 217-220 (or different echo acoustic transducers) such that they may provide a return echo signal in response. One will recognize that various numbers of transmit/receive acoustic transducers and echo acoustic transducers may be used and the disclosure herein is not limited to any particular number described or shown herein.

The transmit/receive acoustic transducer 13 and the echo acoustic transducer 17 (or the transducers as described with reference to FIG. 7) may be implanted and/or otherwise associated with any medium that transmits sound (e.g., such as shown generally by medium 16 in FIG. 1, which may be, for example, tissue, such as heart tissue, vascular tissue, etc., or any other structural elements associated with the body of a patient) for taking measurements in various applications. For example, such transducers may be implanted for taking measurements of the cardiovascular system (e.g., such as aortic measurements, atrial measurements, ventricular measurements, etc.) for use, for example, in determining stroke volume, or for determining any other parameter associated with the heart, may be implanted for taking measurements associated with the urinary tract or bladder, may be implanted for taking measurements associated with the digestive tract, etc. As shown in the flow diagram of FIG. 3, one or more distance measurements may be made (block 93) (e.g., with respect to such medium 16) and one or more different therapies may be carried out using such distance measurements (block 95). For example, various therapies have been described herein for various conditions (e.g., stimulation therapy, drug therapy, etc.).

Figure 4:
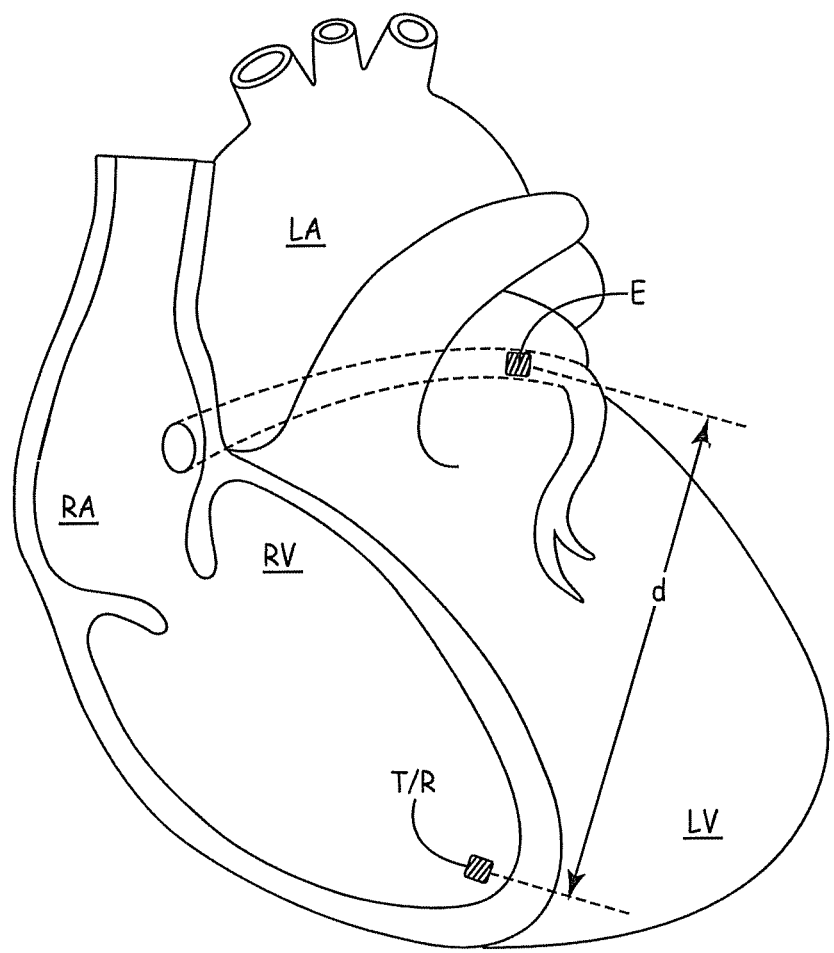
FIG. 4 is an exemplary diagram illustrating an enlarged view of a heart including acoustic sensors implanted therein for use in carrying out a distance measurement.
Figure 5:
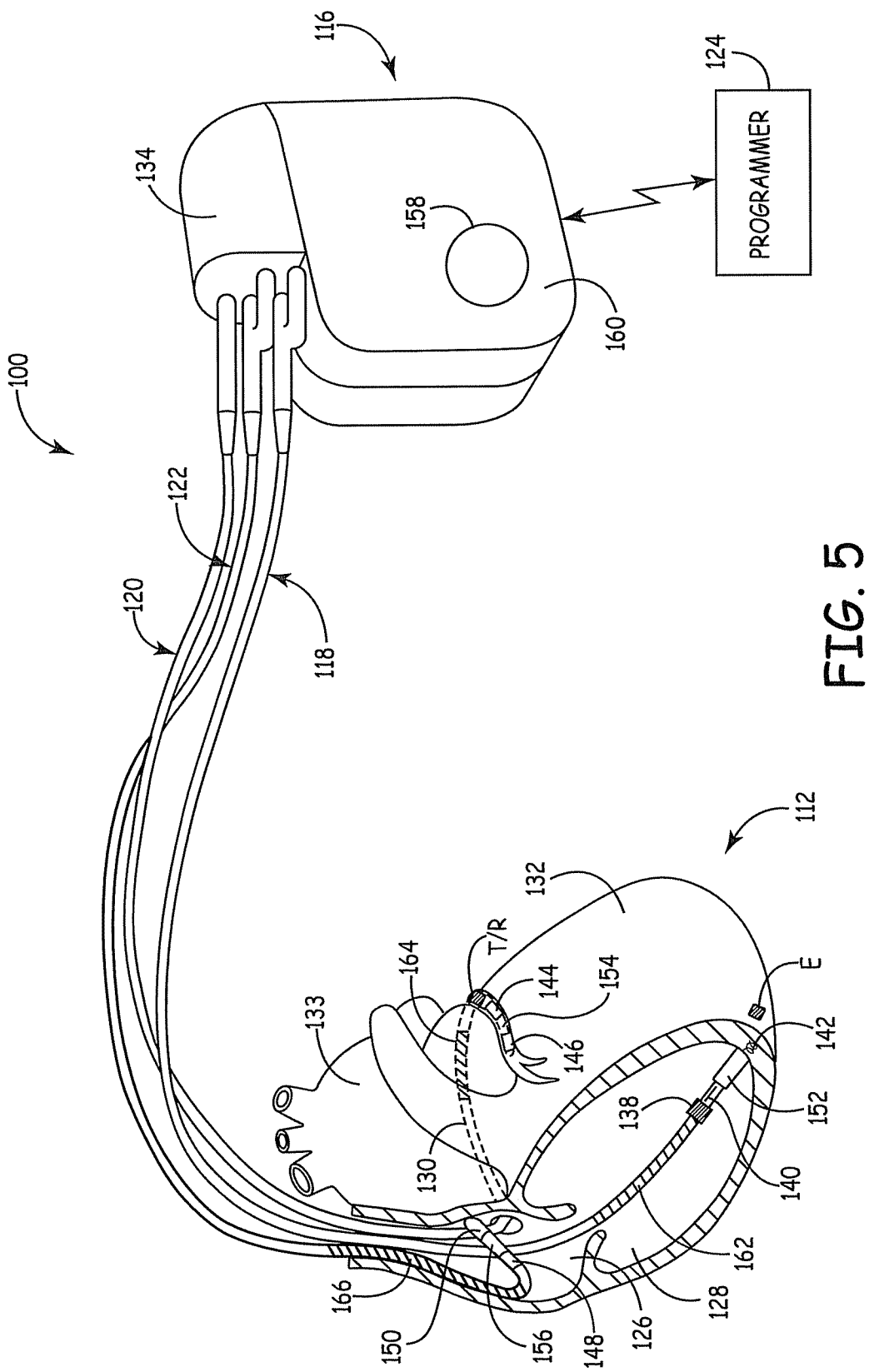
FIG. 5 is a general diagram illustrating an example therapy system that provides therapy to a patient based on one or more distance measurements.
Figure 6:
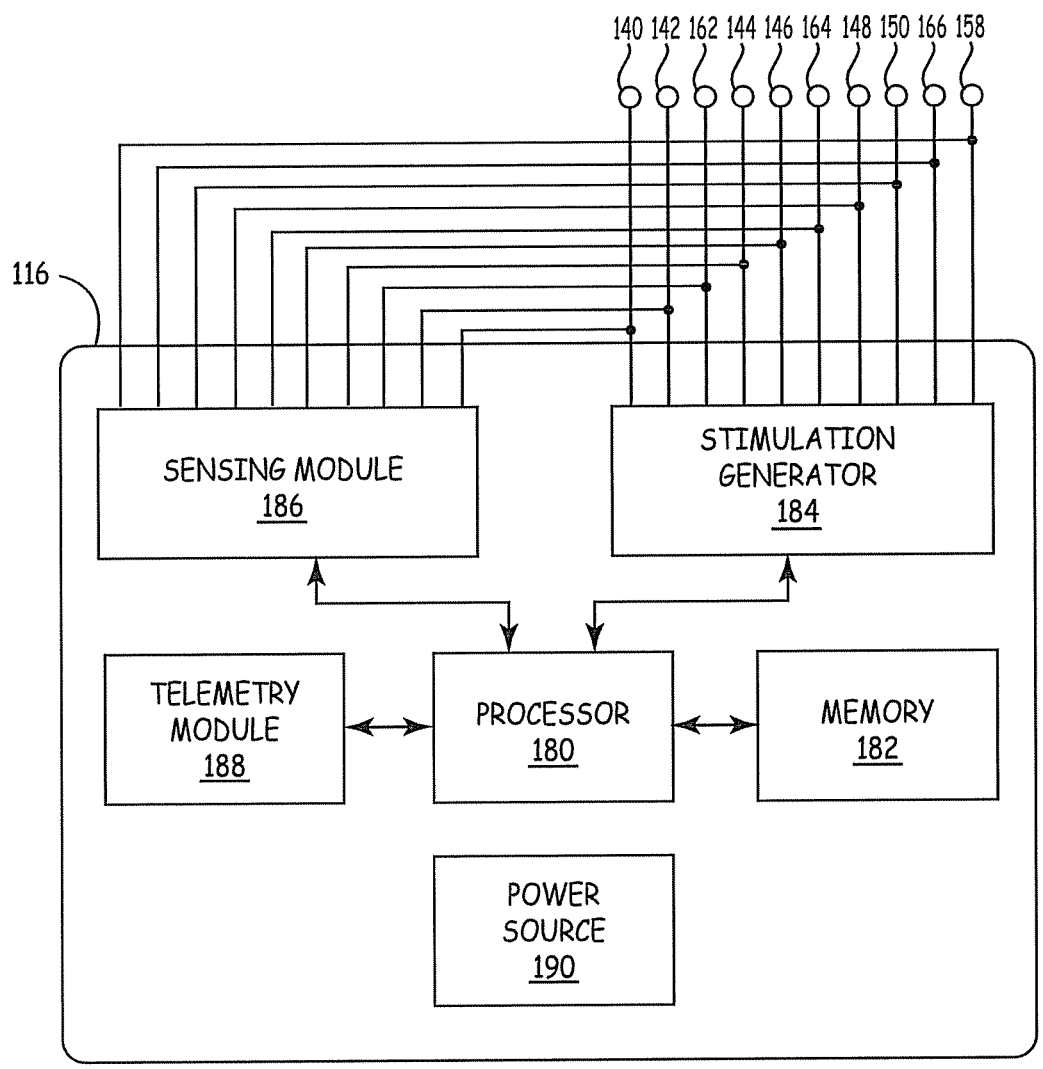
FIG. 6 is a functional block diagram of one example configuration of an implantable medical device that may implement a measurement process as shown, for example, in FIG. 2.

One embodiment of an implantable medical device and system which may use distance measurement information determined as described herein is shown in FIGS. 4-6. FIG. 4 illustrates the sonomicrometry technique described herein for measuring a left ventricular dimension. As shown, transducers such as piezoelectric sonomicrometer crystals, are placed in two locations that span a portion of the left ventricle. Other acoustic sensors having the ability to transmit and receive acoustic signals as described herein may also be used. The left ventricular dimension is produced by measuring the time delay as described herein. The locations for placement of the transducers may be, for example, implanted in the right ventricular apex and the distal coronary sinus using a lead or guide wire or guide catheter. Various locations may be chosen, for example, the transducers may be placed on the outside of the heart (e.g., using epicardial leads) such that the two transducers span a portion of the left ventricle, or the transducers may be placed directly on the epicardium or endocardium without a specific pacing lead. In this embodiment, once positioned, the two transducers should remain in fixed locations relative to the heart such that measurements of left ventricle dimensions share a common reference and can be compared. However, it is also envisioned that such transducers may be moved.

FIG. 4 illustrates one embodiment of a distance measurement method herein with relation to the heart using sonomicrometry crystals as the transducers. An electric potential is applied to one of the piezoelectric sonomicrometry crystals (T/R), creating vibrations and sending sound pulses toward the receiving echo crystal (E), which detects the pulses and generates a return echo pulse to be detected by crystal (T/R) which detects the return echo pulse and generates an electric potential induced by the vibrations. The distance between the crystals (d) is calculated as previously described herein based on the transmit time of the pulse from crystal (T/R) and the receive time of the return echo pulse detected by crystal (T/R).

FIGS. 5-6 show a general conceptual diagram illustrating an example therapy system 100 including components for carrying out distance measurements as described herein that may be used to provide therapy to heart 112 of a patient (e.g., ordinarily, but not necessarily, a human). Therapy system 100 includes implantable medical device 116, which is coupled to leads 118, 120, and 122, and may be coupled to a programmer (124). IMD 116 may be, for example, an implantable pacemaker, cardioverter, and/or defibrillator that provide electrical signals to heart 112 via electrodes coupled to one or more of leads 118, 120, and 122.

Leads 118, 120, 122 extend into the heart 112 of a patient to sense electrical activity of heart 112 and/or deliver electrical stimulation to heart 112. In the example shown in FIG. 5, right ventricular (RV) lead 118 extends through one or more veins (not shown), the superior vena cava (not shown), and right atrium 126, and into right ventricle 128. Left ventricular (LV) coronary sinus lead 120 extends through one or more veins, the vena cava, right atrium 126, and into the coronary sinus 130 to a region adjacent to the free wall of left ventricle 132 of heart 112. Right atrial (RA) lead 122 extends through one or more veins and the vena cava, and into the right atrium 126 of heart 112.

IMD 116 may sense electrical signals attendant to the depolarization and repolarization of heart 112 via electrodes coupled to at least one of the leads 118, 120, 122. In some examples, IMD 116 provides pacing pulses to heart 112 based on the electrical signals sensed within heart 112 (as well as distance measurements made of certain heart dimensions). The configurations of electrodes used by IMD 116 for sensing and pacing may be unipolar or bipolar. IMD 116 may also provide defibrillation therapy and/or cardioversion therapy via electrodes located on at least one of the leads 118, 120, 122. IMD 116 may detect arrhythmia of heart 112, such as fibrillation of ventricles 128 and 132, and deliver defibrillation therapy to heart 112 in the form of electrical pulses. In some examples, IMD 116 may be programmed to deliver a progression of therapies, e.g., pulses with increasing energy levels, until a fibrillation of heart 112 is stopped. IMD 116 detects fibrillation employing one or more fibrillation detection techniques known in the art.

In some examples, programmer 124 may be a handheld computing device or a computer workstation. Programmer 124 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 124 can additionally or alternatively include a peripheral pointing device, such as a mouse, via which a user may interact with the user interface. In some embodiments, a display of programmer 124 may include a touch screen display, and a user may interact with programmer 124 via the display.

A user, such as a physician, technician, or other clinician, may interact with programmer 124 to communicate with IMD 116. For example, the user may interact with programmer 124 to retrieve physiological or diagnostic information from IMD 16, such as distance measurements made by the system. A user may also interact with programmer 124 to program IMD 16, e.g., select values for operational parameters of the IMD.

For example, the user may use programmer 124 to retrieve information from IMD 116 regarding the rhythm of heart 112, trends therein over time, or tachyarrhythmia episodes. As another example, the user may use programmer 124 to retrieve information from IMD 16 regarding other sensed physiological parameters of patient 114, such as intracardiac or intravascular pressure, activity, posture, respiration, distance measurements, such as relating to left ventricle, thoracic impedance, etc. As another example, the user may use programmer 124 to retrieve information from IMD 116 regarding the performance or integrity of IMD 116 or other components of system 100, such as leads 118, 120, and 122, or a power source of IMD 116.

The user may use programmer 124 to program a therapy progression, select electrodes used to deliver defibrillation shocks, select waveforms for the defibrillation shock, or select or configure a fibrillation detection algorithm for IMD 116. The user may also use programmer 124 to program aspects of other therapies provided by IMD 116, such as cardioversion or pacing therapies. In some examples, the user may activate certain features of IMD 116 by entering a single command via programmer 124, such as depression of a single key or combination of keys of a keypad or a single point-and-select action with a pointing device.

IMD 116 and programmer 124 may communicate via wireless communication using any techniques known in the art. Examples of communication techniques may include, for example, low frequency or radiofrequency (RF) telemetry, but other techniques are also contemplated. In some examples, programmer 124 may include a programming head that may be placed proximate to the patient's body near the IMD 116 implant site in order to improve the quality or security of communication between IMD 116 and programmer 124.

Leads 118, 120, 122 may be electrically coupled to a stimulation generator, a sensing module, or other modules IMD 116 via connector block 134. In some examples, proximal ends of leads 118, 120, 122 may include electrical contacts that electrically couple to respective electrical contacts within connector block 134. In addition, in some examples, leads 118, 120, 122 may be mechanically coupled to connector block 134 with the aid of set screws, connection pins or another suitable mechanical coupling mechanism.

Each of the leads 118, 120, 122 includes an elongated insulative lead body, which may carry a number of concentric coiled conductors separated from one another by tubular insulative sheaths. In the illustrated example, a pressure sensor 138 and bipolar electrodes 140 and 142 are located proximate to a distal end of lead 118. In addition, bipolar electrodes 144 and 146 are located proximate to a distal end of lead 120 and bipolar electrodes 148 and 150 are located proximate to a distal end of lead 122. In FIG. 5, pressure sensor 138 is disposed in right ventricle 128. Pressure sensor 138 may respond to an absolute pressure inside right ventricle 128, and may be, for example, a capacitive or piezoelectric absolute pressure sensor. In other examples, pressure sensor 138 may be positioned within other regions of heart 112 and may monitor pressure within one or more of the other regions of heart 112, or may be positioned elsewhere within or proximate to the cardiovascular system of patient 114 to monitor cardiovascular pressure associated with mechanical contraction of the heart.

Electrodes 140, 144 and 148 may take the form of ring electrodes, and electrodes 142, 146 and 150 may take the form of extendable helix tip electrodes mounted retractably within insulative electrode heads 152, 154 and 156, respectively. Each of the electrodes 140, 142, 144, 146, 148 and 150 may be electrically coupled to a respective one of the coiled conductors within the lead body of its associated lead 118, 120, 122, and thereby coupled to respective ones of the electrical contacts on the proximal end of leads 118, 120 and 122.

Electrodes 140, 142, 144, 146, 148 and 150 may sense electrical signals attendant to the depolarization and repolarization of heart 112. The electrical signals are conducted to IMD 116 via the respective leads 118, 120, 122. In some examples, IMD 116 also delivers pacing pulses via electrodes 140, 142, 144, 146, 148 and 150 to cause depolarization of cardiac tissue of heart 112. In some examples, IMD 116 includes one or more housing electrodes, such as housing electrode 158, which may be formed integrally with an outer surface of hermetically-sealed housing 160 of IMD 116 or otherwise coupled to housing 160. In some examples, housing electrode 158 is defined by an uninsulated portion of an outward facing portion of housing 160 of IMD 116. Other division between insulated and uninsulated portions of housing 160 may be employed to define two or more housing electrodes. In some examples, housing electrode 158 comprises substantially all of housing 160. Any of the electrodes 140, 142, 144, 146, 148 and 150 may be used for unipolar sensing or pacing in combination with housing electrode 158. As described in further detail with reference to FIG. 6, housing 160 may enclose a stimulation generator that generates cardiac pacing pulses and defibrillation or cardioversion shocks, as well as a sensing module for monitoring the patient's heart rhythm.

Leads 118, 120, 122 also include elongated electrodes 162, 164, 166, respectively, which may take the form of a coil. IMD 116 may deliver defibrillation shocks to heart 112 via any combination of elongated electrodes 162, 164, 166, and housing electrode 158. Electrodes 158, 162, 164, 166 may also be used to deliver cardioversion pulses to heart 112. Electrodes 162, 164, 166 may be fabricated from any suitable electrically conductive material, such as, but not limited to, platinum, platinum alloy or other materials known to be usable in implantable defibrillation electrodes.

Pressure sensor 138 may be coupled to one or more coiled conductors within lead 118. In FIG. 5, pressure sensor 138 is located more distally on lead 118 than elongated electrode 162. In other examples, pressure sensor 138 may be positioned more proximally than elongated electrode 162, rather than distal to electrode 162. Further, pressure sensor 138 may be coupled to another one of the leads 120, 122 in other examples, or to a lead other than leads 118, 120, 122 carrying stimulation and sense electrodes. In addition, in some examples, pressure sensor 138 may be self-contained device that is implanted within heart 112, such as within the septum separating right ventricle 128 from left ventricle 132, or the septum separating right atrium 126 from left atrium 133. In such an example, pressure sensor 138 may wirelessly communicate with IMD 116.

Still further as shown in FIG. 5, an acoustic sensor including a transmit/receive acoustic transducer T/R is provided for implantation using a lead in a similar manner to incorporation of the pressure sensor 138. As shown in FIG. 5, transducer T/R may be implanted using lead 120 and electrically coupled to IMD 116 using lead 120 for providing acoustic pulses such as described herein. However, at least in one embodiment, transmit/receive acoustic transducer T/R may be a self-contained device that is implanted within heart 112. In such an example, transmit/receive acoustic transducer T/R may wirelessly communicate with IMD 116.

Likewise, an echo acoustic sensor including an echo acoustic transducer E is also provided for implantation. Although a lead may be used to provide the echo acoustic transducer E in a similar manner to incorporation of the pressure sensor 138, at least in one embodiment the echo acoustic transducer E is a self-contained device that is implanted within heart 112 and configured to provide a return echo pulse as described herein.

In such an example, echo acoustic transducer E may wirelessly communicate with IMD 116 and/or transmit/receive acoustic transducer T/R.

The configuration of therapy system 100 illustrated is merely one example. In other examples, a therapy system may include epicardial leads and/or patch electrodes instead of or in addition to the transvenous leads 118, 120, and 122. Further, IMD 116 need not be implanted within patient 114. In examples in which IMD 116 is not implanted in patient 114, IMD 116 may deliver defibrillation shocks and other therapies to heart 112 via percutaneous leads that extend through the skin of patient 114 to a variety of positions within or outside of heart 112. However, the acoustic transducers T/R and E would be implanted to provide distance measurement information to the IMD 116.

In other examples of therapy systems that provide electrical stimulation therapy to heart 112, a therapy system may include any suitable number of leads coupled to IMD 116, and each of the leads may extend to any location within or proximate to heart 112. For example, other examples of therapy systems may include three transvenous leads located as illustrated in FIG. 5, and an additional lead located within or proximate to left atrium 133. Other examples of therapy systems may include a single lead that extends from IMD 116 into right atrium 126 or right ventricle 128, or two leads that extend into a respective one of the right ventricle 126 and right atrium 128.

FIG. 6 is a functional block diagram of one example configuration of IMD 116, which includes processor 180, memory 182, stimulation generator 184, sensing module 186, telemetry module 188, and power source 190 (e.g., such components similar to those described with reference to FIG. 1). Processor 180 controls stimulation generator 184 to deliver stimulation therapy to heart 112 according to a selected one or more of therapy programs, which may be stored in memory 182, and based on one or more different parameters (e.g., such as the distance measurements described herein). Specifically, processor 180 may control stimulation generator 184 to deliver electrical pulses with the amplitudes, pulse widths, frequency, or electrode polarities specified by the selected one or more therapy programs using electrically coupled electrodes 140, 142, 144, 146, 148, 150, 158, 162, 164, and 166 (e.g., using a switch module to select appropriate electrodes).

Sensing module 186 monitors signals from at least one of electrodes 140, 142, 144, 146, 148, 150, 158, 162, 164 or 166 in order to monitor electrical activity of heart 112, e.g., via electrocardiogram (ECG) signals. Sensing module 186 may also include a switch module to select which of the available electrodes are used to sense the heart activity. In response to the signals from processor 180, the switch module of within sensing module 186 may couple the outputs from the selected electrodes to one of the sensing channels. Further, for example, in response to the signals from processor 180, operation of the transmit/receive acoustic transducer T/R and echo acoustic transducer E are controlled for use in carrying out the measurement process described herein.

Telemetry module 188 may include any suitable hardware, firmware, software or any combination thereof for communicating with another device, such as programmer 124. Under the control of processor 180, telemetry module 188 may receive downlink telemetry from and send uplink telemetry to programmer 124 with the aid of an antenna, which may be internal and/or external. Processor 180 may provide the data to be uplinked to programmer 124 and the control signals for the telemetry circuit within telemetry module 188, e.g., via an address/data bus. In some examples, telemetry module 188 may provide received data to processor 180 via a multiplexer.

The various components of IMD 116 are coupled to power source 190, which may include a rechargeable or non-rechargeable battery. A non-rechargeable battery may be selected to last for several years, while a rechargeable battery may be inductively charged from an external device, e.g., on a daily or weekly basis.

During operation, IMD 116 may collect, measure, and store various forms of diagnostic data, such as distance measurements as described herein. In certain cases, IMD 116 may directly analyze collected diagnostic data and generate any corresponding reports or alerts. In some cases, however, IMD 116 may send diagnostic data to programmer 124, and/or another external device (e.g., wirelessly) for remote processing and analysis.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. An implantable medical device measurement system comprising:
    a transmit/receive acoustic sensor comprising a transmit/receive acoustic transducer implantable at a first location, wherein the transmit/receive acoustic transducer is configured to transmit and receive acoustic signals;
    an echo acoustic sensor comprising an echo acoustic transducer implantable at a second location, wherein the echo acoustic transducer is configured to receive an acoustic signal from the transmit/receive acoustic transducer and in response thereto transmit a return echo signal to be received by the transmit/receive acoustic transducer; and
    a controller configured to control transmission of the acoustic signal from the transmit/receive acoustic transducer at a transmit time and determine a receive time corresponding to the time the transmit/receive acoustic transducer receives the return echo signal transmitted by the echo acoustic transducer, wherein the controller is further configured to determine a distance between the transmit/receive acoustic transducer and the echo acoustic transducer as a function of the transmit time and the receive time.

2. The system of claim 1, wherein the controller configured to determine a distance between the transmit/receive acoustic transducer and the echo acoustic transducer as a function of the transmit time and the receive time determines a distance between the transmit/receive acoustic transducer and the echo acoustic transducer using the relationship of distance $d = V_{sound} \times \Delta t / 2$, where $\Delta t$ is the time between the transmit time and the receive time, and $V_{sound}$ is the velocity of the acoustic signals traveling between the transmit/receive acoustic transducer and the echo acoustic transducer.

3. The system of claim 1, wherein the system further comprises a therapy device to provide a therapy to a patient based at least in part on the distance determined between the transmit/receive acoustic transducer and the echo acoustic transducer.

4. The system of claim 1, wherein the system comprises an implantable medical device and at least the transmit/receive acoustic transducer is part of a lead to be implanted.

5. The system of claim 1, wherein the transmit/receive acoustic transducer is connected to the control module by a wire connection, and further wherein the echo acoustic sensor comprises a wireless echo acoustic sensor.

6. The system of claim 5, wherein the wireless echo acoustic sensor comprises power circuitry to provide power to allow the echo acoustic sensor to detect the receipt of the acoustic signal from the transmit/receive acoustic transducer and to transmit the return echo signal in response thereto.

7. The system of claim 1, wherein the system further comprises one or more additional acoustic transducers implantable at further additional locations, wherein each of the additional acoustic transducers is configured to receive the acoustic signal from the transmit/receive acoustic transducer and in response thereto transmit a return echo signal to be received by the transmit/receive acoustic transducer for use in determining a distance between the transmit/receive acoustic transducer and each of the additional acoustic transducers.

8. The system of claim 7, wherein each of the additional acoustic transducers is configured to receive the acoustic signal from the transmit/receive acoustic transducer and in response thereto transmit a return echo signal at a different frequency to be received by the transmit/receive acoustic sensor for use in determining a distance between the transmit/receive acoustic transducer and each of the additional acoustic transducers.

9. The system of claim 7, wherein at least one of the one or more additional acoustic transducers to be implanted at further additional locations is configured to transmit an acoustic signal to one or more of the other additional acoustic transducers and receive a return echo signal therefrom for use in determining a distance between the at least one additional acoustic transducers and each of the one or more other additional acoustic transducers providing a return echo signal.

10. The system of claim 1, wherein each of the transmit/receive acoustic sensor and echo acoustic sensor comprise one or more sonomicrometry piezoelectric crystals.

11. An implantable medical device method of measuring distance using implantable acoustic transducers, comprising:
    implanting a transmit/receive acoustic transducer at a first location, wherein the transmit/receive acoustic transducer is configured to transmit and receive acoustic signals;
    implanting an echo acoustic transducer at a second location, wherein the echo acoustic transducer is configured to receive an acoustic signal from the transmit/receive acoustic transducer and transmit a return echo signal in response thereto to be received by the transmit/receive acoustic transducer;
    transmitting an acoustic signal from the transmit/receive acoustic transducer at a transmit time;
    detecting, using the echo acoustic transducer, the acoustic signal transmitted by the transmit/receive acoustic transducer and transmitting a return echo signal to be received by the transmit/receive acoustic sensor;
    receiving, using the transmit/receive acoustic transducer, the return echo signal transmitted by the echo acoustic transducer at a receive time; and
    determining a distance between the transmit/receive acoustic transducer and the echo acoustic transducer as a function of the transmit time and the receive time.

12. The method of claim 11, wherein determining the distance between the transmit/receive acoustic transducer and the echo acoustic transducer as a function of the transmit time and the receive time comprises determining a distance between the transmit/receive acoustic transducer and the echo acoustic transducer using the relationship of distance $d = V_{sound} \times \Delta t/2$, where $\Delta t$ is the time between the transmit time and the receive time, and $V_{sound}$ is the velocity of the acoustic signals traveling between the transmit/receive acoustic transducer and echo acoustic transducer.

13. The method of claim 11, wherein the method further comprises providing a therapy to a patient based at least in part on the distance determined between the transmit/receive acoustic transducer and the echo acoustic transducer.

14. The method of claim 11, wherein implanting the transmit/receive acoustic transducer at a first location comprises implanting the transmit/receive acoustic transducer as part of a lead of an implantable medical device.

15. The method of claim 11, wherein implanting the echo acoustic transducer at a second location comprises implanting a wireless acoustic transducer at the second location.

16. The method of claim 11, wherein the method further comprises implanting one or more additional wireless acoustic transducers at further additional locations, wherein each of the additional wireless acoustic transducers is configured to receive the acoustic signal from the transmit/receive acoustic transducer and in response thereto transmit a return echo signal to be received by the transmit/receive acoustic transducer for use in determining a distance between the transmit/receive acoustic transducer and each of the additional wireless acoustic transducers.

17. The method of claim 16, wherein the method further comprises receiving, by each of the additional wireless acoustic transducers, the acoustic signal from the transmit/receive acoustic transducer and in response thereto transmitting, by each of the additional wireless acoustic transducers, a return echo signal at a different frequency to be received by the transmit/receive acoustic transducer for use in determining a distance between the transmit/receive acoustic sensor and each of the additional wireless acoustic transducers.

18. The method of claim 11, wherein the method further comprises implanting one or more additional acoustic transducers at further additional locations, wherein at least one of the one or more additional acoustic transducers implanted at further additional locations is configured to transmit an acoustic signal to one or more of the other additional acoustic transducers and receive a return echo signal therefrom for use in determining a distance between the at least one additional acoustic transducers and each of the one or more other additional acoustic transducers providing a return echo signal.

19. An implantable medical device system comprising:
transmit/receive acoustic sensor means comprising a transmit/receive acoustic transducer to be implanted at a first location for transmitting and receiving acoustic signals;
echo acoustic sensor means comprising an echo acoustic transducer to be implanted at a second location for receiving an acoustic signal from the transmit/receive acoustic transducer and in response thereto transmitting a return echo signal to be received by the transmit/receive acoustic transducer;
control means for controlling transmission of the acoustic signal from the transmit/receive acoustic transducer at a transmit time and determining a receive time corresponding to the time the transmit/receive acoustic transducer receives the return echo signal transmitted by the echo acoustic transducer, wherein the control means further comprises means for determining a distance between the transmit/receive acoustic transducer and the echo acoustic transducer as a function of the transmit time and the receive time.

* * * * *